Oct. 12, 1948. M. E. FRANCISCO Plant Pat. 808
APRICOT TREE
Filed Dec. 16, 1946
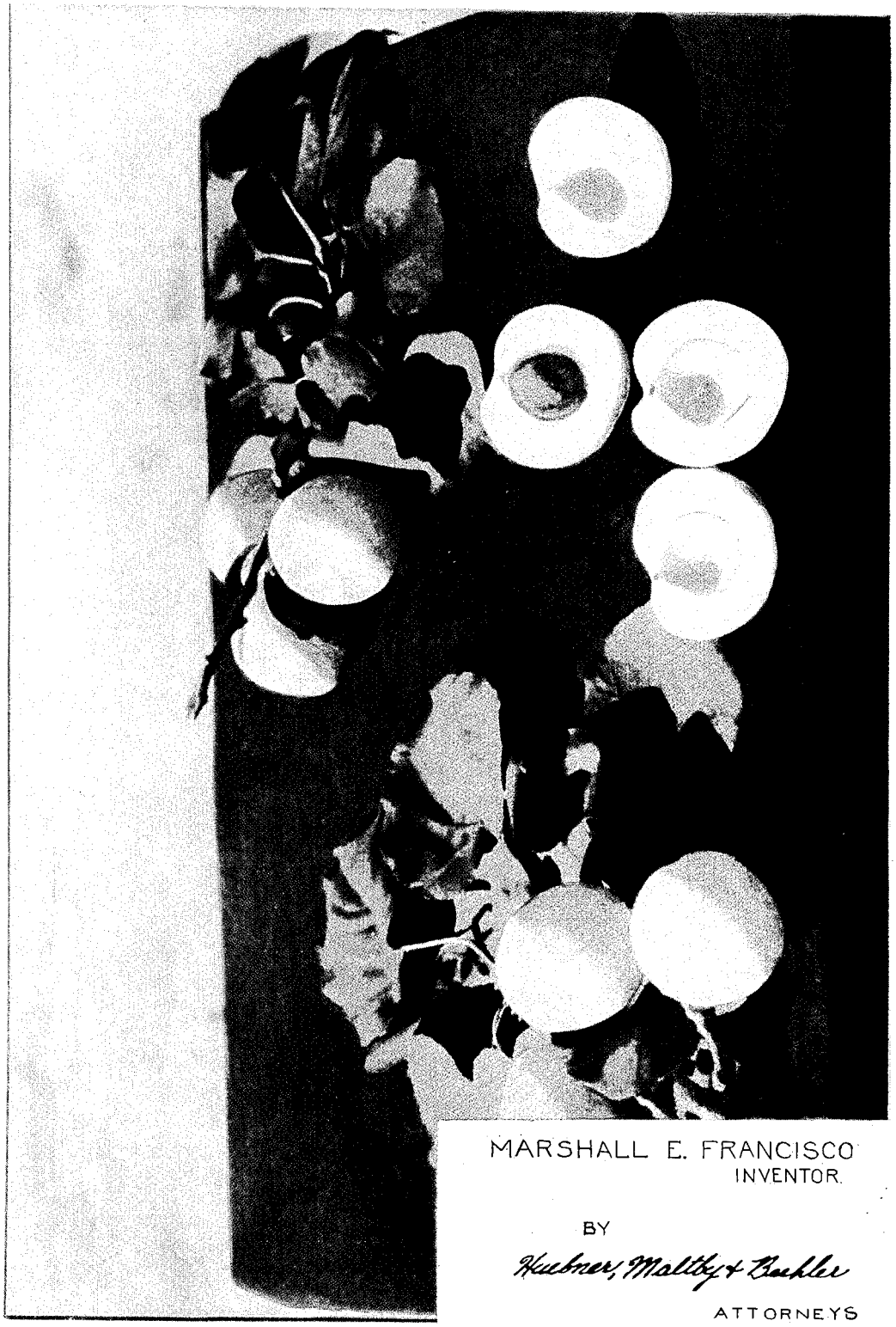
MARSHALL E. FRANCISCO
INVENTOR.
BY
Huebner, Maltby & Beehler
ATTORNEYS Patented Oct. 12, 1948

Plant Pat. 808

UNITED STATES PATENT OFFICE

808

APRICOT TREE

Marshall E. Francisco, Fresno, Calif.

Application December 16, 1946, Serial No. 716,589

1 Claim. (Cl. 47—62)

The present invention relates to a plant invention or discovery and more particularly to a new variety of apricot tree.

The production of apricots in the San Joaquin Valley of California and other areas having similar warm and dry summers and winters of at least infrequent freezing temperatures presents many problems to the grower, processor and shipper. Freezing weather has the effect of impeding the formation and maturation of a crop. Excessive heat and low humidity, although valuable in the drying of the fruit, cause conventional apricots to ripen prematurely, to develop adscititious coloring, to spoil near the pit and to develop other characteristics undesirable in apricots. Under ideal conditions, present known apricots have shipped poorly. During hot weather apricots cannot be transported any great distance without refrigeration.

These and other problems have motivated a quest by the present inventor, covering many years of work with apricots, having the following objectives:

To provide an improved variety of apricot tolerant to drouth and excessive heat.

To provide a frost resistant apricot tree.

To provide superior fruit of improved flavor, having a high sugar content, a good appearance, good shipping qualities, and improved drying and canning characteristics in a variety of apricot of the character described.

To provide a disease resistant apricot tree having vigorous growing habits.

It is submitted that these and other objectives apparent in the following description have been achieved by the new variety of apricot of the present application.

The drawing of the present application consists of a colored photograph of clusters of apricots and fruit bearing branches of the new variety, showing in addition, characteristic fruit bisected for inspection.

The origin of the new variety apricot is a seedling originally intended as root stock and suited to the purpose by its vigorous growing habits and disease resistant qualities, presently more fully described. The parentage of the seedling is not certain, but the seed is believed to have been from a Tilton. The new variety first attracted attention in an orchard of Tilton apricots. The seedling had been budded to a Tilton. A wire bearing a name tag attached to the trunk of the young tree slipped down and as the tree grew, girdled it at, or just below, the union of the Tilton scion and the root stock. The claimed variety of apricot is believed to have grown from an adventitious bud arising from the girdling wound. The vigorous growth of the seedling was noted by the present applicant who carefully cultivated, tested, developed, and asexually reproduced the improved variety of apricot over a period of twelve years from the time of its discovery until the present patent application. The characteristics of the original discovery are in all respects similar to those of its asexual reproductions.

The tree of the improved apricot is of medium size, grows vigorously but not with unusual speed, and produces fruit at an average age for apricot trees.

The tree of the new variety of apricot is somewhat larger than the Tilton, the commercial variety that it most nearly resembles. In silhouette, the new variety is characterized by a generally rounded top portion, spreading branches, dense foliage, and vigorous growth. Referring in detail to the leaves of the trees shown in the drawing, the foliage of the new variety is characteristically darker green in color than is commonly observed in apricot trees and appears fresh and luxuriant.

The buds in the dormant season are normally 1½ times as large as the buds of conventional apricot trees and generally are formed in pairs or triads, the leaf buds almost never occurring on fruit wood in the absence of fruit buds. The blossoms are of characteristic apricot form but occur slightly more profusely than is generally known in apricots. The present variety is apparently not subject to fruit drop. The blossoms are slightly pinkish white, about an inch across, practically sessile and generally appressed. They occur at or about blooming time of the Tiltons.

Apricot trees, being one of the earliest fruit trees to blossom, are often injured by frost. Although Tiltons are usually the last to reach full bloom, even they have an occasional crop ruined by a late frost. The new variety blooms at about the same time as the Tiltons but according to past experience is not harmed by the frost. On one occasion, an entire orchard of Tiltons had its crop destroyed by frost. Three trees of the new variety, scattered widely through the Tilton orchard, and in bloom at the same time, produced a normal crop. This is believed to be due, at least in part, to the unusually large size of the buds of the new variety of apricot and the stocky fruit wood. Further climatic tolerance has been observed for the present variety. The tree itself can withstand excessive heat and periods of drouth without injury. The fruit ripens naturally in excessive heat, acquiring its natural color and retaining its characteristic firmness of flesh, presently more fully described. The fruit resists sunburn, is not scaly and does not crack.

The fruit of the new species is somewhat similar to the Tilton, but differs therefrom in certain particulars. It is much larger, roundish ovate in shape, concave at the stem end, only slightly compressed and of substantially uniform halves. The suture is shallow, but clearly defined. The skin is smooth and delicate in texture and is only very finely pubescent, approaching a glabrous condition. The fruit ripens evenly over the entire tree and each fruit ripens evenly to a uniform deep golden yellow and in some districts may be tinged with red. The even ripening of the fruit over the entire tree is a valuable asset at picking time. Fewer pickings are required to harvest the entire crop with resultant reductions in harvest expenses. The uniformity of ripening of each apricot is of obvious commercial advantage.

The flesh, when mature, is bright orange, juicy, possesses a rich, luscious flavor and is generally of a higher sugar content than the Tilton. It dries much heavier than the Tilton or any other commercial variety of apricot grown in this area and available for comparison.

Generally apricots ripen from the inside out and thus, because of their maturity and tender character, are easily damaged in handling and shipping by the time they are colored sufficiently to harvest. The present species ripens from the outside inwardly and is maturely colored while still of firm flesh. Such fruit are of good flavor, high sugar content, and are not easily damaged by handling and shipping. In experiments directed to the testing of the shipping quality of this new apricot, quantities of the fruit have been wrapped and shipped successfully by rail express, without benefit of refrigeration, for distances in excess of 1,000 miles and the fruit found to arrive in perfect condition. The shipping quality of this new apricot is superior to the shipping qualities of the currently well known varieties. Attention is respectfully directed to the fact that the greatly improved shipping qualities are apparently due to the manner of ripening and firm quality of the flesh and not primarily to the skin, which is thin and delicate.

The stone of the new apricot is ovate, flattened and much smaller than the Tilton. At maturity the stone occupies only a portion of the pit-well. It is blunt at the dorsal end and apex, channeled part way along its back and has three longitudinal ridges. The ridges are not nearly as sharp as those of the Tilton. In this respect the stone of the new variety is similar to the Blenheim, although less than half as large. The flesh clings to the stone only along the ridges. As in the Moorpark and Hemskirke, the stone presents a singular character in being longitudinally perforated and having fibrovascular bundles passing therethrough. This characteristic is not deemed dependable for the perforations are minute and not always present. Like the Moorpark a needle may be inserted through the dorsal end of the stone. The kernel is bitter; less so than the Shipley apricot and more so than the Breda or Angoumois.

The leaves of the present variety of apricot, as shown in the drawing, comprise a blade portion and a petiole. The petiole is long, is grooved longitudinally, and has conspicuous glands. There are no stipules. The blade portion closely approaches a circular form having a subcordate base and a clearly cuspidate apex. The periphery of the blade is serrated. The leaf is thicker and heavier than is usually found in apricots and is larger, the leaves frequently exceeding twice the length and twice the breadth of a Tilton apricot leaf grown in a similar environment. This is clearly apparent in Fig. 1. The surfaces of the leaf are rugose. The leaf is pinnately veined. The secondary veins separate from the midrib in sharp, clear-cut angles. The reticulations between the secondary veins are net-veined in character. The nodes are alternate, as shown in Fig. 2, and unusually large.

The trunk and branches of the tree are medium stocky and the bark and lenticels characteristic of apricot trees in general. The fruit wood is short and stubby. A year's growth of fruit wood is normally only one or two inches long, but heavy, being stub-like in form. Among other advantages, this reduces pruning expenses and breaking from overloading during fruit season.

For purposes of more clearly describing and defining the new variety of apricot, comparisons are drawn with well known varieties, as follows:

The new variety properly thinned, frequently produces fruit of a size requiring only 6 to 8 to weigh a pound. The fruit is similar to the Moorpark in size, coloring, and somewhat in flavor. It is somewhat less compressed and has a less distinct suture. Other illustrative differences are, the present species bears fruit of uniformly equal halves, produces regular crops and ripens its fruit evenly. Both varieties are vigorous growers.

The fruit of the new variety is similar to that of the Royal and Blenheim in color and in evenness of ripening, but is shaped more like the Tilton. It ripens at or about the time of the Blenheims, the latter part of June or first of July, but is distinguished therefrom by being a more regular producer and having a free stone.

Like the Hemskirke, the fruit of the new variety is large, round, of even halves, richly colored, and ripens evenly. It bears more abundantly than the Hemskirke and is not subject to the preripened drop of the latter.

The fruit somewhat resembles the Derby in color and shape, but ripens about two weeks later.

The fruit of the new variety contrasts with the Newcastle in that it is larger, about a month later in ripening, has a much firmer flesh and has much improved shipping qualities. Present tests have not been conclusive, but have been generally indicative of a tolerance to warm winter weather, it, like the Newcastle, seldom shows any indication of delayed foliation.

Like the Stewart, the present species produces large, round, ovate fruit of rich color and has a firm flesh, but does not possess the Stewart's exacting soil requirements nor the Stewart's tendency to produce fruit of irregular and variable shape. Quite in contrast to the Stewart, the present apricot is very tolerant to poor soil, succeeding in sizing well without fertilizer, and the fruit is markedly uniform in shape.

As previously discussed, the new variety has outstanding shipping qualities, being of firm flesh and ripening from the outside inwardly, it is picked when fully colored and carries well. When dried, it is thick, heavy, and orange in color, being more golden than the Tilton. The pit well dries to an orange color as distinguished from white for the Tilton. Having a thin skin, firm flesh and good flavor, it is excellently suited to canning, tending to mush only upon excessive cooking. It buds and grafts easily. The new variety apparently is resistive to the fungus growth *Coryneum beijerinckii* commonly known as "shot hole." The evidence available is not conclusive, but trees of the present variety growing in an apricot orchard subject to "shot hole" have displayed only minor effects thereof. Ripening from the outside inwardly, no instance of "pit scald" has been found in the present variety. Grown in zinc deficient soil with Tiltons, the trouble known as "little leaf" did not appear in the present variety but markedly affected the Tiltons. Twelve years of experimentation with the present apricot indicates that it is resistive, if not immune, to *Sclerotinia fructicola* commonly known as "brown rot."

The hardiness of this variety in its resistance to cold, heat, drouth, and disease; its vigorous growing habits; and its fruit of outstanding shipping, drying, and canning qualities are outstanding characteristics.

Having clearly described the new and improved apricot tree, what I claim is:

The variety of apricot tree herein described and illustrated characterized particularly by large fruit buds in the dormant stage; by its vigorous growing habits, by tolerance to heat and cold; by its heavy production of fruit of superior size and color; by the fruit's firmness of flesh and resulting superior shipping, drying, and canning qualities; and by the fruit's ripening from the outside inwardly as distinguished from the reverse procedure commonly known in apricots.

MARSHALL E. FRANCISCO.

No references cited.